(12) United States Patent
Gueck et al.

(10) Patent No.: US 7,338,449 B2
(45) Date of Patent: Mar. 4, 2008

(54) THREE DIMENSIONAL LOCATOR FOR DIAGNOSTIC ULTRASOUND OR MEDICAL IMAGING

(75) Inventors: Wayne J. Gueck, Redmond, WA (US); John C. Lazenby, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 294 days.

(21) Appl. No.: 10/854,002

(22) Filed: May 25, 2004

(65) Prior Publication Data

US 2005/0267364 A1    Dec. 1, 2005

(51) Int. Cl.
*A61B 8/00*    (2006.01)

(52) U.S. Cl. ....................... 600/447; 128/916

(58) Field of Classification Search ........ 600/443–447, 600/454–458; 128/916; 73/625–626
See application file for complete search history.

(56) References Cited

U.S. PATENT DOCUMENTS 4,580,054 A * 4/1986 Shimoni ................ 250/363.04
5,465,721 A * 11/1995 Kishimoto et al. .......... 600/443
5,538,003 A * 7/1996 Gadonniex et al. .......... 600/445
5,608,849 A * 3/1997 King, Jr. ..................... 345/419
6,047,080 A * 4/2000 Chen et al. .................. 382/128
6,110,111 A * 8/2000 Barnard ....................... 600/438
6,464,642 B1 * 10/2002 Kawagishi ................... 600/454
6,600,475 B2   7/2003 Gutta et al. .................. 345/156

OTHER PUBLICATIONS

EP1308903 Kim publ. May 07, 2003.*
WO/097/50058 Goto et al publ. Dec. 31, 1997.*

* cited by examiner

*Primary Examiner*—Francis J. Jaworski

(57) ABSTRACT

A location within a volume is determined from medical images. A region of interest or other location is examined from two different viewing directions. The user or processor indicates the region or point of interest in each of the different images. The desired point or region within the three-dimensional volume is determined from the intersection of two lines, each line parallel to the viewing direction of a respective image and passing through the selected point or region of each image. The identified location within the volume is used for any of various purposes, such as for measurements associated with a distance between two points or selection of a region of interest including the selected point as part of a border or within the region.

35 Claims, 3 Drawing Sheets

THREE DIMENSIONAL LOCATOR FOR DIAGNOSTIC ULTRASOUND OR MEDICAL IMAGING

BACKGROUND

The present invention relates to locating a region within a three-dimensional volume. For two-dimensional medical imaging, the distance between two points is easily determined. The endpoints are readily identified within the scan plane of the image, such as by user selection, and the scan parameters are used to identify a distance between the two points. Similarly, the user can assist in determining a region of interest by selecting one or more points along the desired border. Since the scan plane associated with the image is well defined, identification of points or other regions within the scan plane may be made with minimal error in reference to the patient location. However, two-dimensional representations of a three-dimensional (3D) volume introduce ambiguity. Since the 3D volume is viewed on a two-dimensional device, selection of a position on the image corresponds to a plurality of different locations. For a given pixel, the pixel locations on the viewing display represents a line in a viewing direction used for rendering the representation of the three-dimensional volume.

BRIEF SUMMARY

By way of introduction, the preferred embodiments described below include methods and systems for determining a location or locations within a volume from medical images. A region of interest or other location is examined from two different viewing directions. The user or processor identifies the region or point of interest in each of at least two different images, each representing the region or point from non-parallel viewing directions. A point within the three-dimensional volume is then defined by the intersection of two lines, each line along the viewing direction of a respective image and passing through the selected point of each image. When the image is an orthogonal projection, the line along the viewing direction is parallel to the viewing direction since the perspective point is taken out to infinity. When the image is a perspective projection, the line along the viewing direction is exactly that, the line through both the perspective point and the selected point on the image. A collection of points within the three-dimensional volume is defined by the intersections of collections of lines, each line along the viewing direction of a respective image and passing through selected points of each image. For example, a region within the three-dimensional volume is defined by the intersections of the collection of lines, each line along the viewing direction of a respective image and passing through the points of a region selected from each image. The identified location within the volume is used for any of various purposes, such as for measurements associated with a distance between two points, a length of arc determined by the intersection of two surfaces, an area defined as the surface of a volume or the intersection of a surface of a volume, or a volume determined by the intersection of two volumes; or selection of a region of interest including the selected point as part of a border or within the region.

In a first aspect, a method is provided for determining a location within a volume from ultrasound images. A line associated with a first ultrasound image at a first viewing direction is identified. Another line associated with a second ultrasound image at a second viewing direction different than the first viewing direction is also identified. The location is determined as a function of the two lines.

In a second aspect, a method for determining a location within a volume for medical images is provided. A first point is identified on a first medical image representing a three-dimensional volume at a first viewing direction. The first viewing direction is rotated to a second viewing direction. A second point is identified on a second medical image representing the three-dimensional volume at the second viewing direction. The location within the three-dimensional volume is determined as a function of the two identified points.

In a third aspect, a system is provided for determining a location within a volume from medical images. A memory is operable to store data representing a three-dimensional volume. A three-dimensional image processor is operable to render medical images from the data as a function of different viewing directions. A location processor is operable to identify a location within the three-dimensional volume as a function of two lines associated with a respective two medical images at different viewing directions.

In a fourth aspect, a method is provided for making a measurement within a volume from ultrasound images. A first line associated with a first ultrasound image at a first viewing direction is identified. A second line associated with a second ultrasound image at a second viewing direction different than the first viewing direction is identified. A first location is determined as a function of the first and second lines. The identification and determination acts are repeated until enough locations are determined to make the measurement. For example, arcs, surfaces or volumes are determined from the repetitions for making an associated measurement.

In a fifth aspect, a method is provided for improving a measurement within a volume from ultrasound images. The method of the fourth aspect or another method is used multiple times, each time creating an associated measurement. The multiple measurements are combined to create a statistically improved measurement.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts through the different views.

DETAILED DESCRIPTION OF THE DRAWINGS AND PRESENTLY PREFERRED EMBODIMENTS

To completely resolve ambiguity of a location within a volume represented by a two-dimensional image, two different viewing directions are used. The point of interest is selected in both viewing directions. In one embodiment, a line along the viewing direction passing through the selected points in one image intersects a line along the viewing direction passing through the selected point in the other image within the volume. The intersection of the two lines identifies the desired location. Where inaccuracies due to erroneous position selection, quantization errors or other sources occur, the two lines may pass close to each other without intersection. A point on the line segment of shortest length connecting the two lines is used for identifying the location. For example, the midpoint of the line segment is selected as the determined location within the volume.

In order to further remove inaccuracies in location determination, the location may be determined multiple times using distinct viewing directions for each determination. The multiple locations can be combined to improve the determination of the location. One simple method of combination is to average the various results. More complicated statistical combinations are also possible, such as removal of large variance data from the sample set before averaging.

In order to further remove inaccuracies in measurements, the measurement may be determined multiple times using distinct viewing directions for each determination. The multiple measurements can be combined to improve the determination of the measurement. One simple method of combination is to average the various results. More complicated statistical combinations are also possible, such as removal of large variance data from the sample set before averaging. In some cases, a priori information is available to ensure that the best measurement is the smallest of all measurements made. In other cases, a priori information determines that the best measurement is the largest of all measurements made.

Figure 1:
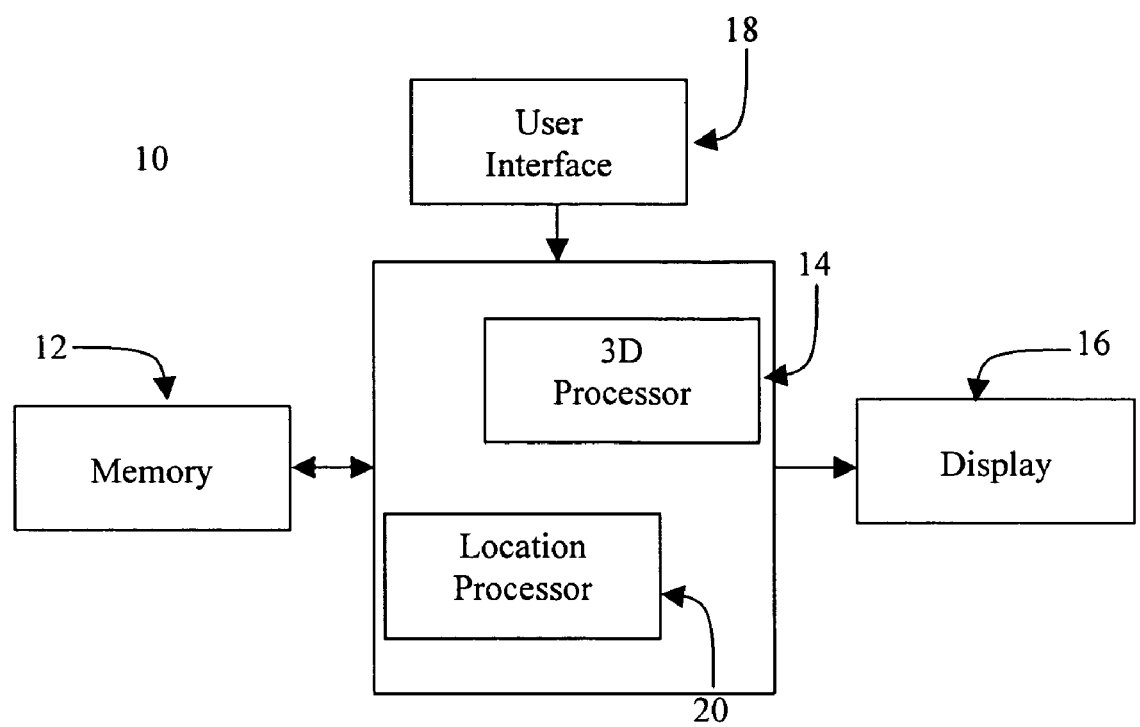
FIG. 1 is a block diagram of one embodiment of a system for determining a location within a volume from medical images.

FIG. 1 shows a system 10 for determining a location within a volume from medical images. The system includes a memory 12, a processor 14, a display 16, a user input 18 and a location processor 20. Additional, different or fewer components may be provided, such as providing the system 10 without the user input 18. In one embodiment, the system 10 is an ultrasound imaging system for both acquisitions of data from a patient as well as three-dimensional rendering of ultrasound images. Alternatively, the system 10 is a workstation which imports data from acquisition systems of any modality. In yet other alternative embodiments, the system 10 operates pursuant to a different modality than ultrasound, such as x-ray, magnetic resonance, computed tomography or positron emission.

The memory 12 is a RAM, ROM, hard drive, removable media, database, buffer, combinations thereof or other now known or later developed device for storing data permanently, temporarily or in a first-in/first-out format. The memory 12 is operable to store data representing a three-dimensional volume. For example, ultrasound data associated with a plurality of planar scans along different planes within a volume is stored as separate frames of data for each plane with corresponding planar position information or stored as a reconstructed or interpolated set of data on a three-dimensional volume grid. Polar or Cartesian coordinate formats may be used. In alternative embodiments, the data representing the three-dimensional volume is stored in any now known or later developed format.

The processor 14 is a general processor, application specified integrated circuit, digital signal processor, video processor, video card, analog circuit, digital circuit, combinations thereof or any other now known or later developed device for rendering a representation from data representing a three-dimensional volume (e.g., a three-dimensional processor). The three-dimensional processor 14 is an image processor operable to render medical images from data as a function of different viewing directions. Any of various rendering techniques now known or later developed may be used, such as alpha blending, maximum intensity projection, minimum intensity projection, surface rendering or selection of an arbitrary plane. For two-dimensional display, the representation of the data representing the three-dimensional volume is rendered with respect to a viewing direction. For an orthogonal projection, each pixel or spatial location within a two-dimensional representation of the three-dimensional volume represents data along a line parallel with the viewing direction, such as an average or a maximum of data along the line. By projecting a viewing direction line along each spatial location or pixel, a two-dimensional representation is rendered as a function of the viewing direction. By orienting the viewing direction to different locations relative to the three-dimensional volume, the same data is rendered to a different image. Similarly, for a perspective projection, each pixel or spatial location within a two-dimensional representation of the three-dimensional volume represents data along the viewing direction, such as an average or a maximum of data along the line.

The display 16 is a CRT, LCD, monitor, projector, plasma screen, television or any other now known or later developed device for displaying an image to a user. The display 16 is operable to display different medical images, such as ultrasound images. Two-dimensional representations rendered from data representing at three-dimensional volume from different viewing directions is output to the display 16. The display 16 displays the two-dimensional representations. For example, the display 16 displays a two-dimensional representation from a particular viewing direction. The display automatically rotates to different viewing directions to assist the user perspective of the three-dimensional volume. As a result, a sequence of two-dimensional representations associated with different viewing directions is repetitively provided to the user on the display 16. Alternatively, the two-dimensional representation or viewing direction is static until a user indicates adjustment to a different viewing direction.

The user input 18 is a trackball, mouse, keyboard, buttons, sliders, knobs, touchpad, combinations thereof or other now known or later developed user input devices. The user input 18 allows control or manipulation of the system 10 by the user. For example, the user inputs a different viewing angle using a numeric keypad or by movement of a cursor with a mouse or trackball. The user input 18 is also operable to receive user selections of regions of interest. For example, the user selects a point, line or two-dimensional shape on a given two-dimensional representation displayed on the display 16. In one embodiment, the user positions a cursor over a desired location, such as a point, and clicks or otherwise activates selection at the current cursor position. A line within an image may be selected by indicating two different points connected by the desired line. Other shapes may be formed by selecting two or more locations and a shape. By selecting different locations on different two-dimensional representations of the three-dimensional volume, the user input 18 provides indications of a desired location within a three-dimensional volume. For example, the user identifies a point or line within each of two or more two-dimensional representations of the three-dimensional volume.

In alternative embodiments, the location processor 20, the three-dimensional processor 14 or another processor is operable to identify locations within an image. For example, an automatic region of interest algorithm is implemented. Thresholding, gradients detection, region growing or other processes may be used to identify a region of interest. A line or location may be identified based on the region of interest. For example, a center of the region of interest is selected by the processor. In alternative embodiments, a combination of user input and automatic processes are performed to identify a point, region or line within a two-dimensional representation. For example, the user indicates one or more points and the processor identifies a region of interest and a point associated with the region of interest.

The location processor 20 is a control processor, general processor, application specific integrated circuit, digital signal processor, analog circuit, digital circuit, combinations thereof or any other now known or later developed device for processing data. The location processor 20 is operable to identify a location within a three-dimensional volume. In response to input from the user input 18 or processing indicating positions of different lines on different images, the location processor determines the location. For example, the location is determined as a function of a first line on a first medical image at a first viewing direction and as a function of a second line of a second medical image at a second viewing direction. In one embodiment, each of the lines extends substantially parallel with the respective viewing directions and pass through indicated points on the respective medical images. In a second embodiment, each of the lines extends substantially along the viewing direction from the perspective point and passing through the indicated points on the respective medical images. In alternative embodiments, one or more of the lines is at a non zero degree angle to the viewing direction, such as being orthogonal to the viewing direction and input as a line within an image or being at a selected angle to the viewing direction that is neither orthogonal nor parallel.

The location processor 20 is operable to identify the location based on the intersection of lines. The lines are non-parallel. Where the lines associated with different images and different viewing directions intersect, the location is at the intersection. Where the lines do not intersect, a line segment along the shortest distance between the two lines is determined. The location is selected as a point along the line segment, such as a midpoint. The location processor 20 may apply a threshold to the shortest distance. Where the shortest distance is larger than the threshold, the process of selecting the lines or identifying the lines is repeated. As an alternative to determining the location within the volume as a point, the location is identified as a sub-volume, such as a region of a desired size around an intersection or a region that includes the shortest distance line segment. One-dimensional, two-dimensional, three-dimensional or a point location is determined using the intersection of the lines. The lines may be included as part of a volume, such as a cylinder extending parallel with the viewing direction for a selected region of interest. The location within the volume is then determined as a point, plane, line, or volume associated with the intersection of two volumes or three-dimensional lines.

The location processor 20 is also operable to determine an one-, two-, or three-dimensional shape as a function of the location. For example, any of the user indicated one-, two-, or three-point locations provides indicators or locations associated with the desired shapes. In additional or alternative embodiments, the identified location is used to further define a shape. For example, the location is used as a node for a region of interest determination. An edge associated with the defined location is then identified within the volume to identify a volume based region of interest. As yet another example, multiple locations are defined and interconnected to define a line segment, a plane or a volume of interest. For example, two points may be used to define a line, cubical, elliptical or spherical shape.

Figure 2:
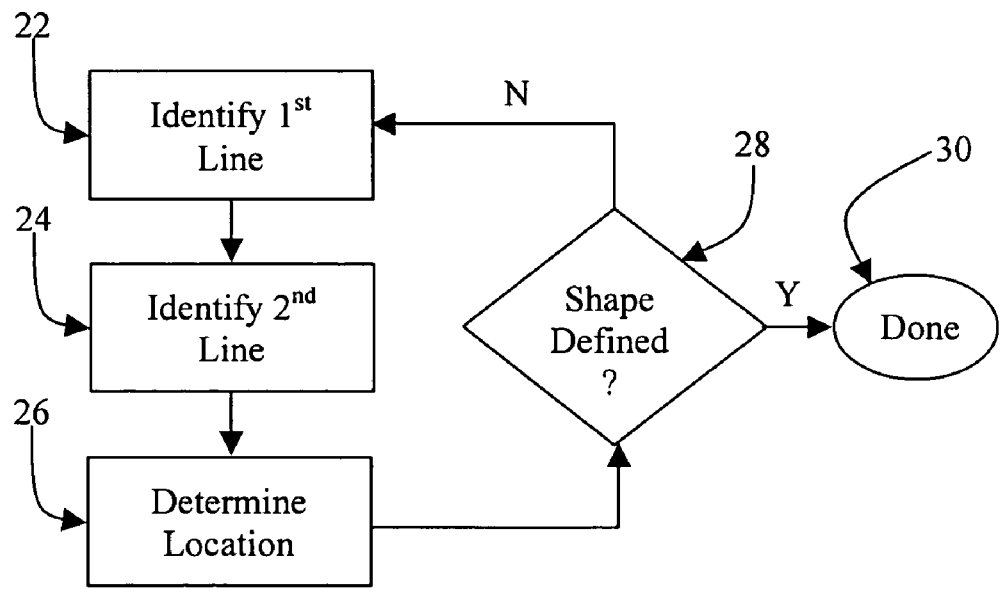
FIG. 2 is a flow chart diagram of one embodiment of a method for determining a location within a volume from medical images.
Figure 3A:
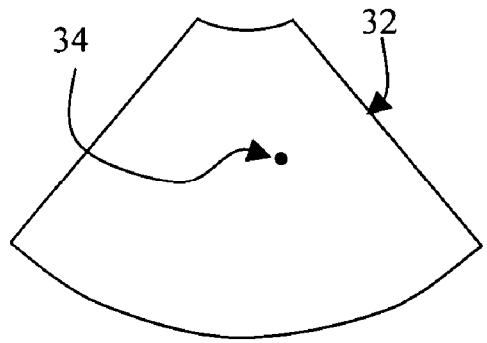
FIGS. 3A and 3B are graphical representations of one embodiment of identifying a point or associating a line with images from different viewing directions.
Figure 3B:
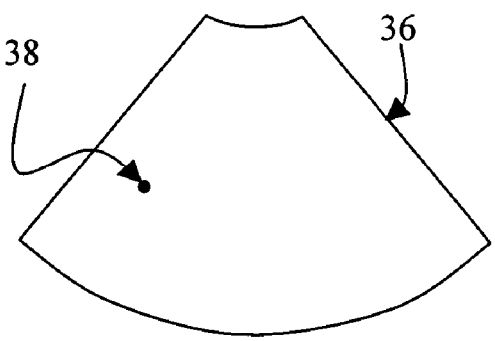

FIG. 2 shows a method of one embodiment for determining a location within a volume from medical or ultrasound images. The method uses the system 10 of FIG. 1 or a different system. Additional, different or fewer acts may be provided in the same or different order. The method of FIG. 2 is described below with additional reference to the graphical representations of FIGS. 3A, 3B and 4. While FIGS. 3A and 3B are shown with a sector shape, such as associated with ultrasound imaging, the images 32, 36 may have any of various shapes.

In act 22, a line is identified. The line is associated with an ultrasound image or other medical image at a first viewing direction. For example, FIG. 3A shows the image 32 as a two-dimensional representation rendered from data representing a three-dimensional volume. In act 24, a different line associated with a different image at a different viewing direction is identified. For example, the image 36 shown in FIG. 3B is a two-dimensional image representing data of a three-dimensional volume at a different viewing direction than associated with the image 32 of FIG. 3A. The difference in viewing directions may be small or large, such as one or a fractional degree through 179 degrees along one or more axes. Each of the images 32 and 36 represent a same three-dimensional volume or are rendered from a same set of data of the volume at different viewing directions. The viewing direction is orthogonal to the image or display plane for an orthogonal projection or from a point spaced from the image for a perspective projection.

In one embodiment, each of the lines is identified by the user defining a line associated with each of the images 32 and 36. Alternatively, the user identifies a volume associated with each of the images 32, 36 and the volumes are used as lines for determining the locations of intersection. In yet another alternative embodiment represented in FIGS. 3A and 3B, the user selects a point 34, 38 on each of the medical images. For example, the user views the image 32 of FIG. 3A and selects the point 34. The user then causes the viewing direction to rotate to a different viewing direction as represented by the image 36. The user then identifies the point 38 in the image 36 representing volume at the different viewing direction. As an alternative to user identification, an automated process is performed to select the points 34 and 38 or regions associated with the points. In yet other alternatives, the two images 32 and 36 with or without additional images are displayed at a same time. An associated line is identified in response to the selection of the points. For example, a line within the three-dimensional volume is identified as substantially parallel to or corresponding with the viewing direction and the selected point within the orthogonal projection. Since the viewing directions are different for the two images 32 and 36, the lines along the viewing direction passing through each of the points 34 and 38 are not parallel to each other. As used herein, "substantially parallel" with the viewing direction accounts for quantization or interpolation differences in constructing a three-dimensional volume set of data or/and rendering a two-dimensional representation from the data. As used herein, "corresponding with" includes a predetermined, selected or other set relationship between the viewing direction and the line.

Figure 4:
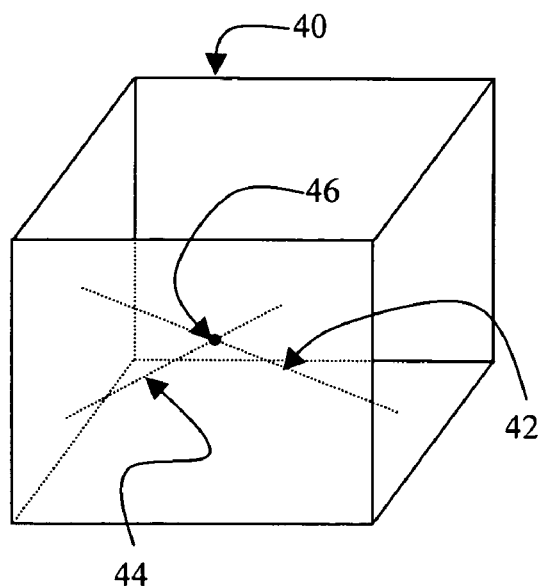
FIG. 4 is a graphical representation showing determination of a region from a plurality of lines within a volume.

In act 26, the location within the three-dimensional volume is determined as a function of two or more lines. Where points are selected to identify the lines, the location within the three-dimensional volume is also determined as a function of two or more points. FIG. 4 shows a volume generally indicated at 40. Two lines 42 and 44 are shown within the volume 40, extending from one edge to another edge. While shown as extending from and to different edge surfaces of the volume 40, the lines 42 and 44 may extend to and/or from a same surface or may be limited in extent to not connect with one or both surfaces. The lines 42 and 44 are shown for conceptual visualization and may or may not be displayed to the user or determined for every location along the lines 42 and 44.

Where the lines 42 and 44 intersect as shown in FIG. 4 at location 46, the location within the volume is determined as the point of intersection 46. For example, the user selected a point corresponding to a desired structure shown in two different images at two different viewing directions. Where the selection is at sufficiently high resolution and accuracy, the lines 42 and 44 intersect. Alternatively, the user selects regions, and extensions of those regions along the viewing direction to volumes represented by the lines 42 and 44 intersect to define a location. Three or more lines may be used to define a location given a common intersection. For example, three different viewing directions are used to define the location within the volume.

Where quantization, resolution, inaccurate placement of the lines or associated points or another source of error results in the lines 42 and 44 not intersecting, the location is determined as a point on a line segment along the shortest distance between the lines 42 and 44. By identifying a line segment having the shortest distance between the two lines 42, 44, a point of closest intersection associated with each of the lines 42, 44 is identified. The desired location then includes a point along the line segment, and may include additional points along or adjacent to the line segment. For example, the location is set as the midpoint along the line segment connecting the lines 42, 44. Where information indicates that the selection associated with one of the lines 42, 44 is more accurate, the determined location may be shifted away from the midpoint, such as closer to the more accurate line 42, 44 or at the intersection of the line segment with the more accurate line 42, 44. The location includes the selected point, or a plurality of points associated with a one-dimensional, two-dimensional or three-dimensional location that includes the selected point. For example, the location is a volume or sub-volume having a predetermined or adaptive size.

The identified location 46 is provided to the user or used by the processor for further calculations. In act 28, a number of identified locations 46 is checked to confirm that the desired shape or use has been provided. For example, a distance between two points within a volume is desired. As a result, a line between two identified locations within the volume is desired. Acts 22, 24 and 26 are repeated for each desired location to be defined within the volume. For distance, two desired locations are determined. A line between the two desired locations is identified or measured as a distance. Two or more determined locations may be used to define a two- or three-dimensional shape. For example, the acts 22, 24 and 26 are repeated to indicate a plurality of locations within the volume. The plurality of locations is then used to define a two- or three-dimensional shape, such as a predetermined shape or a shape defined by interconnecting the identified locations. By repeating the acts twice or three times, a circle may be defined (e.g., two points defining a diameter and location, or a center and radius). The circumference or area of the circle may be measured. By repeating the acts three or more times, an ellipse may be defined (e.g., the longest or shortest diameter is defined by two points with a third point providing a radius from the defined longest or shortest axis, or one point for the center, one point for the long axis radius and another point for the short axis radius). The circumference or area of the ellipse may be measured. The acts may be repeated twice to define a sphere. For example, two points are used to define a diameter/radius/center and location of a sphere. The surface area or volume of the sphere may be measured. An oblate or prolate spheroid may be defined by three or more points and an axis of rotation, or an ellipsoid may be defined by four or more points. Surface areas, volumes, or other characteristics of the shape are measured. Additionally or alternatively, the selected points and/or shapes are displayed to the user.

Figure 5:
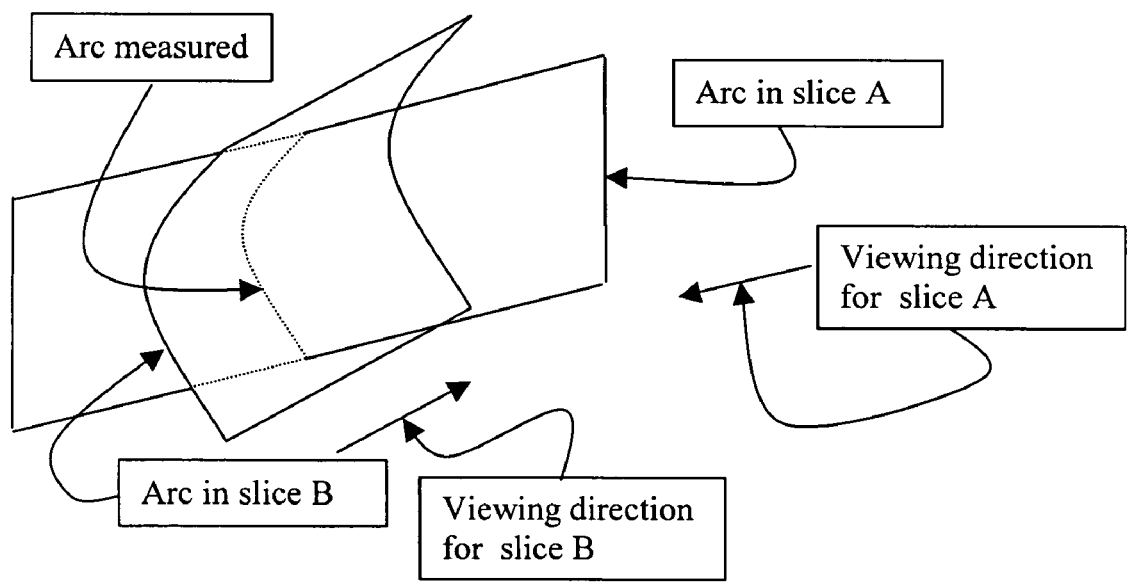
FIG. 5 is a graphical representation showing determination of an arc and a line segment in one embodiment.

Using a plurality of points and associated lines from a fewer number of images and associated viewing directions may be used to determine more complex shapes. For example, FIG. 5 shows defining two arcs (e.g., two straight, two curved or both straight and curved lines) in two different images corresponding to two viewing directions. Each arc or line corresponds to a plurality of points. By projecting the arcs along each of the viewing directions, another arc is defined at the intersection. A characteristic of the arc, such as the length or curvature, is measured. Similarly, an enclosed shape traced by the user or placed by the user on one or more images is projected for defining a line, surface, or volume of intersection. Additionally or alternatively, the selected points and/or shapes are displayed to the user. Any combination of point, arc, enclosed shape or area on one image intersecting with a point, arc, enclosed shape or area from another image with or without projections from additional images may be used.

The identified location or locations within a volume may be used to assist in processor determination of a three-dimensional region of interest. For example, one or more locations are used as nodes in an automatic region of interest determination algorithm. The nodes indicate a surface, gradient or other characteristic within the image to be used to define a region of interest. Using gradients, thresholding, region growing, combinations thereof or other now known or later developed algorithms, the region of interest is defined based on the location or locations. For example, the user selects a tissue boundary, such as the heart wall. Using gradients or thresholds, the boundary is extrapolated within the three-dimensional volume, such as to define a heart chamber.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for determining a point location within a volume from ultrasound images, the method comprising;
   (a) identifying a first line associated with a first ultrasound image at a first viewing direction, the first line extending along the first viewing direction in the volume;

(b) identifying a second line associated with a second ultrasound image at a second viewing direction different than the first viewing direction, the second line extending along the second viewing direction in the volume;

(c) determining the point location as a function of the first and second lines, the point location as a specific point relative to all locations within the volume; and performing a measurement and/or establishing a region of interest as a function of the point location.

2. The method of claim 1 wherein (a) and (b) comprise identifying the first and second lines where the first and second ultrasound images are two-dimensional projection representations of a same three-dimensional volume at the first and second viewing directions.

3. The method of claim 1 wherein (a) comprises:

(a1) selecting a first point on the first ultrasound image; and (a2) identifying the first line as substantially parallel with the first viewing direction and through the first point; and wherein (b) comprises:

(b1) selecting a second point on the second ultrasound image; and (a2) identifying the second line as substantially parallel with the second viewing direction and through the second point.

4. The method of claim 1 wherein (c) comprises determining the location as a point of intersection of the first and second lines.

5. The method of claim 1 wherein (c) comprises determining the location as a point on a line segment, the line segment being a shortest distance between the first and second lines.

6. The method of claim 5 wherein the point is a midpoint on the line segment.

7. The method of claim 1 further comprising:

(d) repeating (a), (b) and (c) for a different location; and (e) identifying a relationship between the location and the different location.

8. The method of claim 1 further comprising:

(d) identifying a three-dimensional region of interest as a function of the location.

9. The method of claim 1 further comprising:

(d) repeating (a), (b) and (c) for at least one additional location; and (e) defining a two or three-dimensional shape as a function of the location and the at least one additional location.

10. The method of claim 1 wherein (c) is repeated and at least some of the multiple locations from the repetition of (c) are combined to determine a single location.

11. The method of claim 1 wherein (c) comprises determining just the point location as a function of both the first and second lines.

12. A method for determining a location within a volume from medical images, the method comprising:

(a) identifying a first point on a first medical image representing a three-dimensional volume at a first viewing direction;

(b) rotating from the first viewing direction to a second viewing direction;

(c) identifying a second point on a second medical image representing the three-dimensional volume at the second viewing direction;

(d) determining the location within the three-dimensional volume as a function of the first and second points, the location determined as a specific location relative to all locations within the volume; and (e) identifying first and second lines within the three-dimensional volume, the first and second lines corresponding respectively to the first and second viewing directions through the first and second points, respectively.

13. The method of claim 12 wherein (d) comprises determining the location as a point of intersection of the first and second lines.

14. The method of claim 12 wherein (d) comprises determining the location as a point on a line segment, the line segment being a shortest distance between the first and second lines.

15. A system for determining a location within a volume from medical images, the system comprising:

a memory operable to store data representing a three-dimensional volume;

a three-dimensional image processor operable to render medical images from the data as a function of different viewing directions; and a location processor operable to identify a point location within the three-dimensional volume as a function of a first line associated with a first medical image at a first viewing direction and a second line associated with a second medical image at a second viewing direction, the point location as a specific point relative to all locations within the volume.

16. The system of claim 15 wherein the location processor is operable to identify the first and second lines as substantially parallel with the first and second viewing directions, respectively, and passing through first and second points on the first and second medical images, respectively.

17. The system of claim 15 wherein the location processor is operable to identify the location as an intersection of the first and second lines.

18. The system of claim 15 wherein the location processor is operable to identify the location as a point on a line segment, the line segment being a shortest distance between the first and second lines.

19. The system of claim 15 wherein the data comprises ultrasound data.

20. The system of claim 15 further comprising:

a display operable to display the first and second medical images; and a user input;

wherein the location processor is responsive to input from the user input indicating first and second positions of the first and second lines.

21. The system of claim 15 wherein the location processor is operable to determine a one, two or three-dimensional shape as a function of the location.

22. A method for making a measurement within a volume from ultrasound images, the method comprising:

(a) identifying a first line associated with a first ultrasound image at a first viewing direction;

(b) identifying a second line associated with a second ultrasound image at a second viewing direction different than the first viewing direction; and (c) determining a first point location as a function of the first and second lines, the point location as a specific point relative to all locations within the volume; and (d) repeating acts (a), (b) and (c) at least once.

23. The method of claim 22 further comprising:

(e) measuring as a function of the first location and at least a second location determined in response to the repetition of (d).

24. The method of claim 23 wherein the steps (a), (b), and (c) are performed twice and the measurement of (e) is a distance measurement.

25. The method of claim 23 wherein the steps (a), (b), and (c) are performed twice and the measurement of (e) is the circumference of a circle.

26. The method of claim 23 wherein the steps (a), (b), and (c) are performed three times and the measurement of (e) is the circumference of an ellipse.

27. The method of claim 23 wherein the steps (a), (b), and (c) are performed twice and the measurement of (e) is the area of a circle.

28. The method of claim 23 wherein the steps (a), (b), and (c) are performed twice and the measurement of (e) is the area of an ellipse.

29. The method of claim 23 wherein the steps (a), (b), and (c) are performed twice and the measurement of (e) is the surface area of a sphere.

30. The method of claim 23 wherein the steps (a), (b), and (c) are performed twice and the measurement of (e) is the volume of a sphere.

31. The method of claim 23 wherein the measurement of (c) is an arc length.

32. The method of claim 23 wherein the measurement of (e) is a surface area.

33. The method of claim 23 wherein the measurement of (e) is a volume.

34. The method of claim 23 wherein (e) is repeated, providing multiple measurements of a same type and further comprising:

(f) combining the multiple measurements as a single measurement.

35. A method for determining a point location within a volume from ultrasound images, the method comprising:

identifying a same region of interest in first and second ultrasound images representing two or three-dimensional portions of the volume, the first and second ultrasound images at different viewing directions relative to the region of interest, the region of interest being within the volume;

determining first and second lines from the identification of the region of interest in the first and second ultrasound images, respectively, and the different viewing directions, the first and second lines having different spatial positions within the volume;

determining the point location within the volume as a function of an intersection or a position closest to intersection of the first and second lines; and defining the region of interest within the volume as a function of the point location.

* * * * *